United States Patent
Littau et al.

(10) Patent No.: US 7,012,049 B2
(45) Date of Patent: Mar. 14, 2006

(54) MULTIPHASE AQUEOUS CLEANSING COMPOSITION

(75) Inventors: Cheryl Littau, Charlotte, NC (US);
Torsten Henning, Bad Soden (DE);
Sandra Porter, Huntersville, NC (US);
Sam Cooper, Charlotte, NC (US)

(73) Assignee: Clariant Finance (BVI) Limited, Tortola (VG)

( * ) Notice: Subject to any disclaimer, the term of this patent is extended or adjusted under 35 U.S.C. 154(b) by 78 days.

(21) Appl. No.: 10/811,362

(22) Filed: Mar. 26, 2004

(65) Prior Publication Data

US 2005/0215443 A1 Sep. 29, 2005

(51) Int. Cl.
*A61K 7/00* (2006.01)
*C11D 1/00* (2006.01)

(52) U.S. Cl. ............ 510/130; 510/137; 510/120; 510/125; 510/159; 510/417; 510/424; 510/428; 510/506; 510/490

(58) Field of Classification Search .......... None
See application file for complete search history.

(56) References Cited

U.S. PATENT DOCUMENTS 5,674,511 A * 10/1997 Kacher et al. ............. 424/401
6,284,230 B1 * 9/2001 Sako et al. ............. 424/70.11
6,429,177 B1 8/2002 Williams et al. ............ 510/130

FOREIGN PATENT DOCUMENTS

WO        WO 02/15849        2/2002

* cited by examiner

*Primary Examiner*—Necholus Ogden
(74) *Attorney, Agent, or Firm*—Richard P. Silverman

(57) ABSTRACT

The present invention relates to a multiphase aqueous cleansing composition for cleansing human skin and hair, which when agitated forms a single application phase, and when left standing, the composition rapidly returns to an appearance having at least two visibly distinct aqueous phases. The multiphase aqueous cleansing composition of the present invention provides an esthetically interesting and useful cleansing composition for use as a body wash, shower gel, foam bath or shampoo. The aqueous multiphase cleansing composition comprises: a surfactant comprising a surfactant or salt thereof; one or more co-surfactants; a humectant; and a salt, wherein the cleansing composition is essentially free of a thickener or a detergent builder.

25 Claims, No Drawings

MULTIPHASE AQUEOUS CLEANSING COMPOSITION

FIELD OF THE INVENTION

The present invention relates to a multiphase aqueous cleansing composition for cleansing human skin and hair, which when agitated forms a single application phase, and when left standing, the composition rapidly returns to an appearance having at least two visibly distinct aqueous phases. More specifically, when agitated, liquid aqueous phases in the multiphase composition are dispersible in one another to form a single application phase, which is a liquid, a dispersion, a lather, or a foam. The multiphase aqueous cleansing composition of the present invention provides an esthetically interesting and useful cleansing composition for use as a body wash, shower gel, bubble bath, hand soap or shampoo.

BACKGROUND OF THE INVENTION

It is known to create a two phase mixture in personal care products. In such multiphase mixtures, one of the phases is an aqueous phase and the other phase will comprise a hydrocarbon oil or other oily substance which is substantially immiscible with the aqueous phase. When agitated, the two phase mixture will distribute itself in a single dispersion and when allowed to settle, the aqueous and oils phases will separate into distinctly separate layers. U.S. Pat. No. 3,718,609 to Weimer, discloses a liquid detergent composition having an aqueous layer and a layer of a liquid, water-immiscible oily material which, when shaken, forms a temporary oil-in-water emulsion. U.S. Pat. No. 3,810,478 to Olson, Jr. et al. discloses a two-phase shampoo composition made by preparing substantially polar and lipophilic portions of a shampoo composition, and mixing them together.

Attempts to create multiphase mixtures which contain aqueous phases have not been successful without the further addition of special purpose components such as thickeners and detergent builders to achieve the multiphase appearance. These compositions consequently comprise components which potentially interfere with the timely separation of the homogenized product back into its aesthetically preferred multiphase aspect, and in some instances (i.e. the use of a detergent builder) when employed in a personal cleanser can actually irritate the skin.

U.S. Pat. No. 6,429,177 to Williams et al. discloses a cleansing system comprising a transparent or translucent package containing a personal product composition having 2 or more visibly distinct phases. When agitated, the composition forms a visible single phase. The composition comprises from 5–35 weight percent surfactant, 1 to 12 weight percent of a thickener, 4 to 20 weight percent of a polyalkylene glycol, and a non-chelating mineral salt which is present in an amount which is sufficient to induce at least two distinct aqueous layers that are present in a volume ratio of upper to lower phase of from 4:1 to 1:4.

EP 0,116,422 (assigned to Reckitt & Coleman) and EP 0,175,485 (assigned to Reckitt & Coleman) disclose multilayer liquid compositions in which two liquids are dispersible and which separate on standing. The compositions require sodium hexametaphosphate as detergent builder to facilitate the formation of the two phases.

In a personal cleansing system for cleansing human skin and hair, a multiphase composition is sought which will provide a clean feeling, which is not oily or greasy, and which leaves no oily or greasy residue on the skin. Furthermore, the multiphase composition must quickly transition between a stable multiphase appearance and upon agitation create a single application phase. In the single application phase, the multiphase composition may be further agitated or intimately mixed by some mechanical device to form a uniformly dispersed or single application phase such as a liquid, a foam or a lather. Still further, after such agitation, the uniformly dispersed phase will quickly return to the stable multiphase appearance.

It is an objective of the present invention to achieve the multiphase appearance of the multiphase composition without employing thickeners (which would retard the separation process unduly) or detergent builders which may irritate the skin and reduce the effectiveness of the multiphase composition as a cleansing composition.

It is an objective of the present invention to provide an aqueous multiphase composition which after agitation and formation of a single application phase, rapidly returns to its multiphase appearance.

SUMMARY OF THE INVENTION

Surprisingly, applicants discovered an aqueous personal cleansing product composition which has the following properties:
when standing, the aqueous personal product composition forms two or more visibly distinct aqueous phases,
when agitated, the composition forms a visible single application phase, and
when left to stand after the aqueous composition has been agitated and has formed the single phase, the aqueous composition will again form two or more visibly distinct aqueous phases, within 12 hours.

The composition comprises a surfactant, a betaine, a co-surfactant, a humectant, a salt, and water. In one embodiment, the composition is an aqueous cleansing composition which comprises:
  a) 2 to 15 wt-% of a surfactant comprising alkali metal salts or ammonium or quaternary ammonium salts of alkyl sulfate or alkyl ether sulfate
  b) 0 to 15 weight percent of a betaine selected from the group consisting of an alkyl betaine; an alkylamido betaine, and mixtures thereof;
  c) 0 to 15 weight percent of a cosurfactant selected from the group consisting of an alkyl ether carboxylic acid or alkali metal or ammonium salt thereof, an acyl glutamate, acylisethioinate and salts thereof, salts of alkylamide ether sulfates, and mixtures thereof;
  d) 2 to 30 weight percent of a humectant comprising a polyethylene glycol;
  e) 12 to 20 weight percent of a salt selected from the group consisting of magnesium sulfate, sodium chloride, potassium chloride, sodium citrate, sodium sulfate, magnesium chloride, and mixtures thereof;

wherein all percentages are based on a total weight of the cleansing composition, wherein the cleansing composition is essentially free of a thickener or a detergent builder. The aqueous multiphase cleansing composition forms a single application phase on agitation and upon cessation of the agitation, the single application phase returns to the multiphase appearance within 8 hours.

It was discovered that to achieve the appearance of 3 distinct phases, it was critical for the composition to include at least a betaine component in the range of from 0.01 to 15 weight percent, and that the ratio of the betaine component to the cosurfactant component also influenced the appearance of a visibly distinct third phase in the multiphase cleansing composition. As a minimum, it was found that the ratio of betaine to the cosurfactant had to be greater than or equal to 0.33:1.

The composition may be dispensed in a clear container such as a bottle or a pump foamer. In using the pump foamer, the multiphase is first agitated and as the agitated phase is pumped, it produces a foam phase which remains stable for the period of its intended use. When returned to a standing state, the agitated phase returned to the multiphase appearance within 12 hours. The composition of the present invention is useful as a cosmetic composition for cleansing human skin or hair, for example, in a shower soap, a hand soap, or a shampoo.

DETAILED DESCRIPTION OF THE INVENTION

The present invention relates to a cleansing system comprising a single chamber transparent package and a personal product composition therein. In an unmixed state, the compositions of the invention will separate into two (or more) stable layers. The upper aqueous layer (for three phase systems the middle aqueous layer) will comprise (a) surfactant; (b) polyalkylene glycol, and/or polyether to improve mildness and separation; (c) electrolyte (non-chelating); and (d) water. The lower layer will have approximately the same ingredients, but the distribution (i.e., % of total component in upper or lower layer) will be different. It is important to emphasize that at least two of the distinct phases are aqueous solutions and that the composition can be prepared without any oil if desired.

More particularly, for the two phase systems, the relative volumes of the upper layer and the lower layer may be anywhere, respectively, from about an 80:20 ratio to about a 20:80 ratio, preferably 70:30 to 30:70, more preferably 60:40 to 40:60. For the three phase systems, the phases are preferably of relatively equal volume (1:1:1) but one of the three phases may be significantly larger or smaller than the other two. It should be noted that ratios are not exact and are highly dependent on composition.

Further, the relative composition of the upper, middle (if present) and lower layers can be described as follows:

The respective distribution of the various components between the layers of a Two Phase System of the present invention can be described as follows:

| Component | Upper Layer | Lower Layer |
|---|---|---|
| Surfactant | 90% or more preferably all * | 10% or lower, preferably substantially absent |
| Polyalkyleneglycol | 75% or greater pref. >80% | 25% or less, preferably <20% |
| Electrolyte (Salt) | 40% or less pref. <35% | 60% or more, preferably >65% |

In the two-layer system of the present invention, the upper phase will comprise at least 90 wt-% surfactant, at least 75 wt-% polyalkyleneglcycol, and less than about 40 wt-% electrolyte, all percentages expressed relative to the total composition. Preferably, in the two-layer system the upper layer will comprise essentially all of the surfactant, at least 80 wt-% of the polyalkyleneglycol, and less than about 35 wt-% of the electrolyte, relative to the total composition. The lower layer of the two-layer system will comprise less than about 10 wt-% surfactant, 25 wt-% or less polyalkyleneglycol, and at least 60 wt-% electrolyte. Preferably, in a two-layer system, the lower layer will be essentially free of surfactant and comprise less than about 20 wt-% polyalkyleneglycol, and at least 65 wt-% electrolyte.

The respective distribution of the various key components between the layers of Three-Layer systems can be described as follows:

| Component | Upper Layer | Lower Layer | Mid. Layer |
|---|---|---|---|
| Surfactant | <5%* | <5% * | ~90% or pref. all |
| Polyalkyleneglycol | 20% or more pref. >30% | 20% or less pref. <15% | >50% pref. >55% |
| Electrolyte (Salt) | <10% pref. <5% | 50% or more pref. >60% | >25% pref. >30% |

In the three-layer system of the present invention, the upper layer will comprise less than or equal to 5 wt-% surfactant, at least 20 wt-% polyalkyleneglcycol, and less than about 10 wt-% electrolyte, all percentages expressed relative to the total composition. Preferably, in the three-layer system the upper layer will comprise essentially no surfactant (less than 1.0 wt-%), at least 30 wt-% of the polyalkyleneglycol, and less than about 5 wt-% of the electrolyte, relative to the total composition. The middle layer of the three-layer system will comprise at least 90 wt-% of surfactant, at least 50 wt-% polyalkyleneglycol, and at least 25 wt-% electrolyte. Preferably, in a three-layer system, the middle layer will comprise essentially all of the surfactant and comprise at least about 55 wt-% polyalkyleneglycol, and at least 25 wt-% of electrolyte. The lower layer of the three-layer system will comprise less than 5 wt-% surfactant, less than or equal to 20 wt-% polyalkyleneglycol, and at least 50 wt-% electrolyte. Preferably, in a three-layer system, the lower layer will comprise less than or equal to 15 wt-% polyalkyleneglycol, and at least 60 wt-% electrolyte.

Each of these components is described in greater detail below.

Surfactant

The surfactant which comprises alkyl ether sulfate salts or alkylsulfate salts generally comprises 2–15% by wt. of the total composition. Preferably, the surfactant comprises 2 to 10 wt-% of the total composition, and more preferably, the surfactant comprises 4 to 9 wt-% of the total composition. The alkyl and alkyl ether sulfates typically have the respective formulae

$ROSO_3M$ and $RO(C_2H_4O)_xSO_3M$ wherein R is alkyl or alkenyl of from about 10 to about 30 carbon atoms, x is from about 1 to about 10, and M is a water-soluble cation such as ammonium, sodium, potassium, magnesium and triethanolamine. Especially preferred for use herein is ammonium lauryl sulfate, ammonium lauryl ether sulfate, sodium lauryl ether sulfate, and mixtures thereof.

Betaines

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, coco betaine (available as Genagen KB from Clariant Corp.), lauryl bis-(2-hydroxyethyl) carboxymethyl betaine, oleyl dimethyl gamma-carboxypropyl betaine, lauryl bis-(hydroxypropyl)alpha-carboxyethyl betaine, and Cocamidopropylbetaine (available as Genagen CAB 818 from Clariant Corp., Charlotte, N.C.)

Cosurfactants

Examples of anionic cosurfactants include sulfonates, isethionates, glutamates, taurates, alkylamide ether sulfates, alkylether carboxylates, mono- or dialkyl phosphate esters and mixtures thereof. The anionic co-surfactants are preferably used in the form of their water-soluble or water-dispersible salts, preferably in the form of the sodium, potassium, magnesium, ammonium, mono-, di- and triethanolammonium and analogous alkylammonium salts. Non-ionic co-surfactants useful herein include those selected form the group consisting of alkyl glucosides, alkyl polyglucosides, polyhydroxy fatty acid amides, alkoxylated fatty acid esters, alcohol ethoxylates, lathering sucrose esters, amine oxides, and mixtures thereof. Non-limiting examples of preferred co-surfactants useful herein include those selected from the group consisting of ammonium cocoyl isethionate, sodium lauroyl isethionate, sodium lauroyl lactylate, triethanolamine lauroyl lactylate, sodium caproyl lactylate, sodium lauroyl sarcosinate, sodium lauroyl methyl taurate, sodium cocoyl methyl taurate, sodium lauroyl glutamate, sodium myristoyl glutamate, and sodium cocoyl glutamate, sodium laureth-13 carboxylate, trideceth-7 carboxylic acid and mixtures thereof.

Humectant

The humectant of the present invention comprises a polyalkylene glycol. The humectant generally comprises 2% to 30% by wt., preferably 5 to 20% by wt. of the total composition. Because the compositions of the invention are personal wash compositions primarily intended for contact with skin during wash, the polyalkylene glycol should be an alcohol, glycol or polyether of minimal molecular weight which is not irritating to the skin. Examples of such include alcohols, particularly polyalkylene oxides having MW 200–6000, preferably including polyalkylene glycol having a molecular weight between 200 to 3000. The polyalkylene glycol can be comprised of ethylene oxide, propylene oxide, butylene oxide or their mixtures either as polymers or copolymers. Specific examples include polyethylene glycols such as Polyglykol 400 (available from Clariant Corporation, Charlotte, N.C.).

Salts

The salt for use in the present invention are salts of alkali metals and/or alkaline earth metals, preferably selected from the group consisting of magnesium sulfate, sodium chloride, potassium chloride, sodium citrate, sodium sulfate, magnesium chloride, and mixtures thereof.

Thickeners

Thickeners are specifically excluded from the composition of the present invention. By the term thickener it is meant, such thickeners which include hydrophobically modified polyethers. Examples of this class of thickeners which may be used include but are not limited to sugar esters such as PEG (160) sorbitan triisostearate or PEG-120 Pentaerythrityl Tetrastearate. Other examples include PEG 120 Methyl Glucose Dioleate; PEG modified glyceryl cocoate, palmate or tallowate. Another class of thickeners are hydrophobically modified cellulose ethers including hydroxyethyl cellulose, hydroxypropylcellulose and cellulose ethers with long pendant chains such as nonoxynyl hydroxyethylcellulose; hydrophobically modified acrylate copolymers such as acrylate/steareth-50 acrylate copolymer; hydrophobically modified polyurethanes; and xanthan gums, guar gums and chemically modified guar gums.

Compositions of the invention have an experiential element in that they are intended to be agitated by the consumer to mix and form a single application phase before separating again after a time, for example, not less than about 15 minutes and not more than about 12 hours.

Packaging

Packages in which the compositions are contained should be translucent or transparent. In practical terms the package should be sufficiently clear or transparent to permit the separation of the two or more layers to be visible to the naked eye.

Optional Components

In addition to the ingredients noted above, the compositions of the invention may contain a variety of optional ingredients or adjuvants including fragrance, dye, antioxidants, chelating agents, moisturizers, active agents (e.g., allantoin), preservatives, antimicrobials and skin conditioners. Skin conditioners may include, but are not limited to polyethylene glycol having a molecular weight greater than about 11,000. A particularly preferred polyethylene glycol is a polyethylene having a molecular weight of about 35,000 (Polyglykol 35000 (INCI: PEG-800), available from Clariant Corporation, Charlotte, N.C.). Other skin conditioners include polypropylene terephthalate, (Aristoflex PEA or Aristoflex PEB-75, available from Clariant Corporation, Charlotte, N.C.), and polymeric quaternary ammonium compounds (e.g. Bozequat 4000, INCI: Polyquaternium-43, available from Clariant Corporation, Charlotte, N.C.).

Except in the operating and comparative examples, or where otherwise explicitly indicated, all numbers in this description indicating amounts or ratios of materials or conditions or reaction, physical properties of materials and/or use are to be understood as modified by the word "about". Where used in the specification, the term "comprising" is intended to include the presence of stated features, integers, steps, components, but not to preclude the presence or addition of one or more features, integers, steps, components or groups thereof.

The method of producing foam is not limited to generating cosmetic foams, but is suitable in general for producing foam, including for an industrial scale. Foam dispensers are understood as meaning all apparatuses which are suitable for the foaming of compositions (mechanic, hydraulic etc.), including those for industrial applications. Preferred foam dispensers are spray containers. Surprisingly, it has been found that some of the compositions are particularly suitable for spraying from mechanical foam dispensers without the need for a propellant gas (e.g. the products "squeeze foamer" and "F2 finger pump foamer" from Airspray International BV). In order to achieve good foam formation, aqueous phases are preferably mixed together mechanically, preferably by simple shaking, prior to foaming.

The following examples are intended to further illustrate the invention and are not intended to limit the invention in any way. Unless indicated otherwise, all percentages are intended to be percentages by weight.

EXAMPLE 1

The following components were mixed together at ambient temperature and the mixture was allowed to settle.

| Component | % wt/wt |
| --- | --- |
| Steol CS-270 (on 100% active basis): | 8.8% |
| Genapol CAB 818 (on 100% active basis): | 5.6% |
| Polyglykol 400 | 17.50% |
| Magnesium sulfate heptahydrate: | 16.40% |
| Nipaguard DMDMH | 0.50% |
| Water: (deionized) | to 100% |

The composition of Example 1 produced 3 visibly distinct phases. The composition was agitated to provide a single application phase. Following the agitation the single application phase was allowed to return to the original multiphase appearance. A bottom phase became visible in 1 hour. The composition separated into to 2 phases in 3 hours, and the composition returned to the appearance of three distinct phases overnight (8–12 hours).

EXAMPLE 2

In Example 2, the following components were mixed together at ambient temperature and the mixture was allowed to settle.

| Component: | % wt/wt |
| --- | --- |
| Steol CS 270 | 13.1% |
| Sandopan DTC Acid | 1.50% |
| Genapol CAB 818 | 14.00% |
| Polyglykol 400 | 17.50 |
| Magnesium sulfate heptahydrate: | 16.40% |
| Nipaguard DMDMH | 0.50% |
| Polyglykol 35000 | 1.00% |
| Aristoflex PEB-75 | 2.00% |
| Water (deionized) | to 100% |

As in Example 1, the composition was agitated to provide a single application phase. Following the agitation the single application phase was allowed to return to the original multiphase appearance. Two layers were visible after about 40 minutes. The original 3 phase appearance returned after the composition of Example 2 was allowed to stand overnight after about 8–12 hours.

EXAMPLE 3

In Example 3, the following components were mixed together at ambient temperature and the mixture was allowed to settle.

| Component: | % wt/wt |
| --- | --- |
| Steol CS 270 (on 100% active basis): | 8.8% |
| Hostapon KCG (on 100% active basis): | 1.25% |
| Genapol CAB 818 (on 100% active basis): | 5.1% |
| Polyglykol 400 | 17.50 |
| Aristoflex PEB-75: | 2.04 |
| Magnesium sulfate heptahydrate: | 16.40% |
| Nipaguard DMDMH | 0.50 |
| Water (deionized) | to 100% |

As in Example 1, the composition of Example 3 was agitated to provide a single application phase. Following the agitation the single application phase was allowed to return to the original multiphase appearance. In Example 3, the original 3 phase appearance returned after the composition of Example 3 was allowed to stand over night. Each of the layers were approximately equal in size. The upper and lower phases were clear and the middle phase was hazy. The upper layer was visible after about 30 minutes, two layers were visible after about 1.5 hours, and the three phase appearance returned after the mixture was allowed to stand overnight, after about 8–12 hours.

EXAMPLE 4

In Example 4, the following components were mixed together at ambient temperature and the mixture was allowed to settle.

| Component: | % wt/wt |
| --- | --- |
| Standapol ES3 (100% active basis): | 8.8% |
| Genapol CAB 818 (on 100% active basis): | 5.6% |
| Polyglykol 400 | 17.5% |
| Polyglykol 35000 | 1.0% |
| Magnesium sulfate heptahydrate: | 16.4% |
| Preservative: | q.s. |
| Water: q.s. | to 100% |

As in Example 1, the composition was agitated to provide a single application phase. Following the agitation the single application phase was allowed to return to the original multiphase appearance. In Example 4, the original 3 phase appearance returned after the composition of Example 4 was allowed to stand over night. The bottom phase became visible in about 2 hours, the mixture separated in to two phases in about three hours, and the 3 layers appearance returned after settling overnight, after about 8–12 hours.

EXAMPLE 5

In Example 5, the following components were mixed together at ambient temperature and the mixture was allowed to settle.

| Component: | % wt/wt |
| --- | --- |
| Standapol ES3 (100% active basis): | 8.8% |
| Genapol CAB 818 (100% active basis): | 5.6% |
| Polyglykol 400 | 17.5% |
| Aristoflex PEA | 2.0% |
| Magnesium sulfate heptahydrate: | 16.4% |
| Preservative: | q.s. |
| Water: q.s. | to 100% |

As in Example 1, the composition of Example 5 was agitated to provide a single application phase. Following the agitation the single application phase was allowed to return to the original multiphase appearance. In Example 5, the original 2 phase appearance returned after the composition of Example 5 was allowed to stand overnight. The bottom layer became visible in about 2 hours, the upper layer was hazy in appearance.

EXAMPLE 6

In Example 6, the following components were mixed together at ambient temperature and the mixture was allowed to settle.

| Component: | % wt/wt |
|---|---|
| Steol CS 270 | 13.1% |
| Sandopan LS-24N | 2.00% |
| Genapol CAB 818 | 14.00% |
| Polyglykol 400 | 17.50 |
| Magnesium sulfate heptahydrate: | 16.40% |
| Nipaguard DMDMH | 0.50% |
| Polyglykol 35000 | 1.00% |
| Aristoflex PEB-75 | 2.00% |
| Water (deionized) | to 100% |

As in Example 1, the composition of Example 6 was agitated to provide a single application phase. Following the agitation the single application phase was allowed to return to the original multiphase appearance. In Example 6, 2 layers appeared within 1 hour after the composition of Example 6 was allowed to stand. Three clear layers were visible after the mixture was permitted to stand overnight, about 8–12 hours.

EXAMPLE 7

In Example 7, the following components were mixed together at ambient temperature and the mixture was allowed to settle.

| Component: | % wt/wt |
|---|---|
| Steol CS 270 | 13.1% |
| Sandopan LS-24N | 4.00% |
| Genapol CAB 818 | 9.35% |
| Polyglykol 400 | 17.50 |
| Magnesium sulfate heptahydrate: | 16.40% |
| Nipaguard DMDMH | 0.50% |
| Polyglykol 35000 | 1.00% |
| Aristoflex PEB-75 | 2.00% |
| Water (deionized) | to 100% |

As in Example 1, the composition of Example 7 was agitated to provide a single application phase. Following the agitation the single application phase was allowed to return to the original multiphase appearance. In Example 7, all 3 layers appeared within 1 hour after the composition of Example 7 was allowed to stand.

EXAMPLES 8–12

Examples 8–12 illustrate (without intending to limit) the wide range of cosurfactants that can be used to achieve the multiphase effect. In Examples 8–12, the following components were mixed together at ambient temperature and the mixtures were allowed to settle. In Experiments 8–12, as shown in Table 1, 2 or 3 layers began to appear within 1 hour after the composition of Examples 8–12 were allowed to stand, although full separation might have taken as long as 8–12 hours.

TABLE 1

Experimental Results 8–12

| Component | Exp. 8 | Exp. 9 | Exp. 10 | Exp. 11 | Exp. 12 |
|---|---|---|---|---|---|
| Steol CS 270 | 13.15 | 13.15 | 13.15 | 13.15 | 13.15 |
| Genagen CAB 818 | 0.0 | 0.0 | 0.0 | 0.0 | 18.0 |
| Hostapon KCG | 0.0 | 0.0 | 0.0 | 0.0 | 5.0 |
| Hostapon SCI-40L | 14.00 | 0.0 | 0.0 | 0.0 | 0.0 |
| Hostapon SCI-85 | 0.0 | 6.30 | 0.0 | 0.0 | 0.0 |
| Genapol AMS | 0.0 | 0.0 | 14.00 | 0.0 | 0.0 |
| Genagen LDA | 0.0 | 0.0 | 0.0 | 18.70 | 0.0 |
| Polyglykol 400 | 17.5 | 17.5 | 17.5 | 17.5 | 17.5 |
| Polyglykol 35000 | 0.0 | 0.0 | 0.0 | 0.0 | 1.0 |
| Aristoflex PEB-75 | 0.0 | 0.0 | 0.0 | 0.0 | 2.0 |
| Bozequat 4000 | 0.0 | 0.0 | 0.0 | 0.0 | 0 |
| Magnesium sulfate heptahydrate | 16.4 | 16.4 | 16.4 | 16.4 | 16.4 |
| Nipaguard DMDMH | 0.5 | 0.5 | 0.5 | 0.5 | 0.5 |
| Water | To 100.0 | To 100.0 | To 100.0 | To 100.0 | To 100.0 |
| Number of phases | 3 | 2 | 2 | 2 | 3 |
| Time required to separate after agitation | 12 hours | 3 hours | 20 min | 12 hours | 30–90 minutes |

TABLE 2

Components Function and Supplier

| Component | Supplier | Function |
|---|---|---|
| Sodium Laureth Sulfate (1, 2, or 3 mol EO) Steol 270 (2 mol), Steol 170 1 mol, Standapol ES-3 (3 mol), Genapol LRO (2 mol) | Stepan Company, Northfield, IL Cognis Corp, Hoboken NJ Clariant Corp., Charlotte, NC. | Surfactant |
| Cocamidopropylbetaine (Genagen CAB 818) | Clariant Corp. Charlotte, NC | Betaine Surfactant |
| Coco-Betaine (Genagen KB) | Clariant Corp. Charlotte, NC | Betaine Surfactant |
| Trideceth-7 Carboxylic Acid (Sandopan DTC Acid) | Clariant Corp. Charlotte, NC | Co-Surfactant |
| Sodium Laureth-13 Carboxylate (Sandopan LS024N) | Clariant Corp. Charlotte, NC | Co-Surfactant |
| Sodium Cocoyl Glutamate (Hostapon KCG) | Clariant Corp. Charlotte, NC | Co-Surfactant |
| Sodium Cocoyl Isethionate (Hostapon SCI 85 or Hostapon SCI-40L) | Clariant Corp. Charlotte, NC | Co-Surfactant |
| Sodium Cocoyl Methyl Taurate (Hostapon CT Paste) | Clariant Corp. Charlotte, NC | Co-Surfactant |
| TEA PEG-3 Cocamide Sulfate (Genapol AMS) | Clariant Corp. Charlotte, NC | Co-Surfactant |
| Sodium Lauroamphoacetate (Genagen LDA) | Clariant Corp. Charlotte, NC | Co-Surfactant |
| Polyethyleneglycol, Avg. MW 400 (Polyglykol 400) | Clariant Corp. Charlotte, NC | Co-Surfactant |
| Polyethyleneglycol, Avg. MW35000 (Polyglykol 35000) | Clariant Corp. Charlotte, NC | Co-Surfactant |
| Polypropylene Terephthalate (Aristoflex PEB-75) | Clariant Corp. Charlotte, NC | Co-Surfactant |
| Polyquaternium-43 (Bozequat 4000) | Clariant Corp. Charlotte, NC | Co-Surfactant |
| Magnesium sulfate heptahydrate | Sigma-Aldrich Corp., St. Louis, MO | Electrolyte |

We claim:

1. An aqueous multiphase cleansing composition having a multiphase appearance with at least two visibly distinct phases, said composition comprising:
   a) 2 to 15 wt-% of a surfactant selected from the group consisting of alkyl ether sulfate and salts thereof, alkyl sulfate and salts thereof and mixtures thereof;
   b) 0.1 to 15 weight percent of a betaine selected from the group consisting of an alkyl betaine, an alkylamido betaine, and mixtures thereof;
   c) A cosurfactant selected from the group consisting of an alkyl ether carboxylic acid or sodium salt thereof, an acyl glutamate, acylisethionate and salts thereof, amide ether sulfate salts, amphoacetates, alkanesulfonate salts and mixtures thereof wherein the ratio of betaine to the co surfactant is at least 0.33 to 1;
   d) 2 to 30 weight percent of a humectant comprising a polyethylene glycol;
   e) 12 to 20 weight percent of a salt selected from the group consisting of magnesium sulfate, sodium chloride, potassium chloride, sodium citrate, sodium sulfate, magnesium chloride, and mixtures thereof;
   wherein all percentages are based on a total weight of said cleansing composition, wherein said cleansing composition is free of a thickener or a detergent builder, and wherein the aqueous multiphase cleansing composition forms a single application phase on agitation and upon suspension of the agitation, the single application phase returns to the multiphase appearance within 12 hours.

2. The aqueous multiphase cleansing composition of claim 1, wherein the betaine comprises 2 to 10 weight percent of said composition.

3. The aqueous multiphase cleansing composition of claim 1, wherein the betaine comprises 2 to 5 weight percent of said composition.

4. The aqueous multiphase cleansing composition of claim 1, wherein the cosurfactant is selected from the group consisting of an alkyl ether carboxylate, an acryl glutamate, and mixtures thereof.

5. The aqueous multiphase cleansing composition of claim 1, wherein the betaine is selected from the group consisting of cocoamido propyl betaine, cocobetaine, and mixtures thereof.

6. The aqueous multiphase cleansing composition of claim 1, wherein the multiphase appearance has 3 visibly distinct phases and wherein the cosurfactant is selected from the group consisting of sodium laureth-13 carboxylate, trideceth-7 carboxylate, and mixtures thereof.

7. The aqueous multiphase cleansing composition of claim 1, wherein the cosurfactant is sodium cocyl glutamate, and a ratio of the betaine to the cosurfactant is greater than 1.5:1, to form 3 visibly distinct phases.

8. The aqueous multiphase cleansing composition of claim 1, wherein the cosurfactant is sodium laureth-13 carboxylate, and a ratio of the betaine to the cosurfactant is greater than 1.1:1, to form 3 visibly distinct phases.

9. The aqueous multiphase cleansing composition of claim 1, wherein the cosurfactant is trideceth-7 carboxylic acid, and a ratio of the betaine to the cosurfactant is greater than 0.33:1, to form 3 visibly distinct phases.

10. The aqueous multiphase cleansing composition of claim 1, wherein the aqueous multiphase cleansing composition has 3 visibly distinct phases.

11. The aqueous multiphase cleansing composition of claim 1, further comprising a skin conditioner selected from the group consisting of a polyethylene glycol having a molecular weight in excess of 11,000, polypropylene terephthalate, a quaternary ammonium conditioning polymer, and mixtures thereof.

12. The aqueous multiphase cleansing composition of claim 1, further comprising an adjuvant selected from the group consisting of fragrances, dyes, antioxidants, chelating agents, moisturizers, active agents, preservatives, skin conditioners, and mixtures thereof.

13. The aqueous multiphase cleansing composition of claim 1, wherein the single application phase is selected from the group consisting of a liquid, a dispersion, and a foam.

14. A method for producing a single application phase from an aqueous multiphase cleansing composition having a multiphase appearance, said method comprising agitating the multiphase cleansing composition having at least two visibly distinct phases to provide the single application phase, wherein the multiphase cleansing composition comprises:
   i) 2 to 15 wt-% of a surfactant selected from the group consisting of alkyl ether sulfate salts, alkylsulfate salts and mixtures thereof;
   ii) 0.01 to 15 weight percent of a betaine selected from the group consisting of an alkyl betaine, an alkylamido betaine, and mixtures thereof;
   iii) A cosurfactant selected from the group consisting of an alkyl ether carboxylic acid or sodium salt thereof, an acyl glutamate, acylisethioinate and salts thereof, and mixtures thereof wherein the ratio of betaine to the co surfactant is at least 0.33 to 1;
   iv) 2 to 30 weight percent of a humectant comprising a polyethylene glycol;
   v) 12 to 20 weight percent of a salt selected from the group consisting of magnesium sulfate, sodium chloride, potassium chloride, sodium citrate, sodium sulfate, magnesium chloride, and mixtures thereof, wherein all percentages are based on a total weight of said cleansing composition, wherein said cleansing composition is free of a thickener or a detergent builder, and wherein the aqueous multiphase cleansing composition forms a single application phase on agitation and upon suspension of the agitation, the single application phase returns to the multiphase appearance within 8 hours.

15. The method of claim 14, wherein the agitation takes place in a non-aerosol pump dispenser when pressure is applied to said dispenser.

16. The method of claim 14 further comprising allowing the single application phase to stand for a time sufficient for said single application phase to return to the multiphase appearance.

17. The method of claim 14, wherein the time is sufficient to return to the multiphase appearance is less than 4 hours.

18. A method for cleansing human skin or hair comprising contacting the human skin or hair with the aqueous composition of claim 1.

19. A cosmetic composition comprising the aqueous multiphase composition of claim 1.

20. A shower soap composition comprising the aqueous multiphase composition of claim 1.

21. A hand soap comprising the aqueous multiphase composition of claim 1.

22. A shampoo comprising the aqueous multiphase composition of claim 1.

23. The aqueous multiphase cleansing composition of claim 1, wherein the salts of alkyl ether sulfate and alkyl sulfate are selected from the group consisting of sodium, ammonium, potassium and mixtures thereof.

24. The aqueous multiphase cleansing composition of claim 1, wherein the salts of acylisethionate are selected from the group consisting of sodium, ammonium, potassium and mixtures thereof.

25. The aqueous multiphase cleansing composition of claim 1, wherein the salts of acylisethionate comprises sodium cocyl isethionate.

* * * * *